(12) United States Patent
Benson et al.

(10) Patent No.: US 8,551,757 B2
(45) Date of Patent: Oct. 8, 2013

(54) *BACILLUS THURINGIENSIS* ISOLATE

(75) Inventors: Terry A. Benson, Spring Grove, IL (US); Samun Dahod, Bristol, WI (US); Ashish Harihar Dave, Wheeling, IL (US); Ayyappan Nair, Des Plaines, IL (US); Regina Adams, Lake Villa, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 350 days.

(21) Appl. No.: 12/879,497

(22) Filed: Sep. 10, 2010

(65) Prior Publication Data

US 2011/0064710 A1 Mar. 17, 2011

Related U.S. Application Data

(60) Provisional application No. 61/241,621, filed on Sep. 11, 2009.

(51) Int. Cl.
*C12N 1/20* (2006.01)
*A61K 38/00* (2006.01)

(52) U.S. Cl.
USPC .................................. 435/252.1; 424/184.1

(58) Field of Classification Search
None
See application file for complete search history.

(56) References Cited

U.S. PATENT DOCUMENTS

| | | | |
|---|---|---|---|
| 4,166,112 A | 8/1979 | Goldberg | |
| 4,766,203 A | 8/1988 | Krieg et al. | |
| 4,935,353 A | 6/1990 | Burges et al. | |
| 5,080,897 A | 1/1992 | Gonzalez et al. | |
| 5,262,159 A | 11/1993 | Payne et al. | |
| 5,262,399 A | 11/1993 | Hickle et al. | |
| 5,273,746 A | 12/1993 | Payne et al. | |
| 5,275,815 A | 1/1994 | Payne | |
| 5,523,211 A | 6/1996 | Pusztai-Carey et al. | |
| 5,801,046 A | 9/1998 | Wilcox et al. | |
| 5,804,180 A | 9/1998 | Baum | |
| 6,210,953 B1 | 4/2001 | Osman et al. | |
| 2003/0049243 A1 | 3/2003 | Liu et al. | |

FOREIGN PATENT DOCUMENTS

| | | |
|---|---|---|
| EP | 0 303 426 B1 | 2/1989 |
| EP | 0 461 799 A2 | 12/1991 |
| EP | 0 480 762 A2 | 4/1992 |
| EP | 0 516 306 A2 | 12/1992 |
| WO | WO 92/19106 | 11/1992 |

OTHER PUBLICATIONS

Hodgman et al., "Characterization of a *Bacillus thuringiensis* strain which is toxic to the housefly musca domestica", FEMS Microbiology Letters 114, 1993, pp. 17-22.
Drummond et al., "Toxicity of *Bacillus thuringiensis* against damalinia ovis (phthiraptera:mallophaga)", Journal of Invertebrate Pathology, 60, 1992, pp. 102-103.
Hofte et al., "Insecticidal crystal proteins of *Bacillus thuringiensis*", Microbiologcal Reviews, Jun. 1989, vol. 53, No. 2, pp. 242-255.
Tailor et al., "Identification and characterization of a novel *Bacillus thuringiensis* δ-endotoxin entomocidal to coleopteran and lepidopteran larvae", Molecular Microbiology, 1992, 6(9), pp. 1211-1217.
Feitelson et al., "*Bacillus thuringiensis*: insects and beyond", Nature Publishing Group, 1992, pp. 271-275.
Crickmore et al., "Revision of the nomenclature for the *Bacillus thuringiensis* perticidal crystal proteins", Microbiology and Molecular Biology Reviews, Sep. 1998, vol. 62, No. 3, pp. 807-813.
Schnepf et al., "The amino acid sequence of a crystal protein from *Bacillus thuringiensis* deduced from the DNA base sequence", The Journal of Biological Chemistry, vol. 260, No. 10, May 25, 1985, pp. 6264-6272.

*Primary Examiner* — Anand Desai
(74) *Attorney, Agent, or Firm* — Wood, Phillips, Katz, Clark & Mortimer

(57) ABSTRACT

A novel bacterial strain of *Bacillus thuringiensis*, VBTS 2528, is described. This strain comprises genes encoding Cry1Ac, Cry 1Ca, and Cry2Aa endotoxin proteins. The invention further relates to an insecticidal composition comprising a mixture of VBTS 2528 and to methods for controlling insect pests utilizing VBTS 2528.

7 Claims, 3 Drawing Sheets

SEQUENCE LISTING

<160> NUMBER OF SEQ ID NOS: 3

<210> SEQ ID NO 1
<211> LENGTH: 120
<212> TYPE: DNA
<213> ORGANISM: Artificial Sequence
<220> FEATURE:
<223> OTHER INFORMATION: DNA Probe for detecting Cry1Ac

<400> SEQUENCE: 1

```
gctacgtcat tagataatct acaatcaagt gattttggtt attttgaaag tgccaatgct      60
tttacatctt cattaggtaa tatagtaggt cttagaaatt ttagtgggac tgcaggagtg     120
```

<210> SEQ ID NO 2
<211> LENGTH: 42
<212> TYPE: DNA
<213> ORGANISM: Artificial Sequence
<220> FEATURE:
<223> OTHER INFORMATION: DNA Probe for detecting Cry1Ca

<400> SEQUENCE: 2

```
cggggattaa ataatttacc gaaatctacg tatcaagatt gg                         42
```

<210> SEQ ID NO 3
<211> LENGTH: 57
<212> TYPE: DNA
<213> ORGANISM: Artificial Sequence
<220> FEATURE:
<223> OTHER INFORMATION: DNA Probe for detecting Cry2Aa

<400> SEQUENCE: 3

```
gactaatctc aatcacaact ttaattgcag cacggtcctc cctcctttat caacacc         57
```

BACILLUS THURINGIENSIS ISOLATE

FIELD OF THE INVENTION

The present invention generally relates to organisms used to produce biological pesticides. More particularly, it relates to a novel strain of the bacterium *Bacillus thuringiensis* which is highly effective against certain insect species, as well as to methods for the preparation and use of this novel strain.

BACKGROUND OF THE INVENTION

Pesticides have enjoyed widespread use in commercial agriculture and have enabled an enormous increase in crop yields and product quality. Pesticides are also routinely used to control various insects, for example, flies or mosquitoes. Often, pest populations pose a nuisance or health hazard to humans or livestock. There is, however, an increasing awareness of environmental risks associated with the use of certain synthetic pesticides, including concern over the bioaccumulation of pesticides in the food chain or their detrimental effects on non-target organisms. Biological pesticides and, especially, natural biopesticides have, therefore, been of considerable interest to those seeking environmentally acceptable means of pest control.

The microorganism *Bacillus thuringiensis* (*B. thuringiensis*) has long been known to be useful in the control of insect pests. The sporulating *B. thuringiensis* cell produces a class of compounds, formerly regarded as a single δ-endotoxin, but now understood to comprise several distinct toxin proteins, which are concentrated in a crystalline protein inclusion body found in the endospore. Upon ingestion of the inclusion body by a susceptible insect larva and proteolysis in the insect gut, the endotoxin proteins are converted into active compounds which destroy the gut epithelium and, ultimately, the pest itself.

*B. thuringiensis* δ-endotoxins have accordingly been found to be useful as pesticides when applied in the form of lysates or other fermentation extracts of cultures of the microorganism.

There are several *Bacillus thuringiensis* strains that are widely used as biopesticides in the forestry, agricultural, and public health areas. *Bacillus thuringiensis* subsp. *kurstaki* and *Bacillus thuringiensis* subsp. *aizawai* produce delta-endotoxins specific for Lepidoptera. A delta-endotoxin specific for Coleoptera is produced by *Bacillus thuringiensis* subsp. *tenebrionis* (Krieg et al., 1988, U.S. Pat. No. 4,766,203). Furthermore, *Bacillus thuringiensis* subsp. *israelensis* produces delta-endotoxins specific for Diptera (Goldberg, 1979, U.S. Pat. No. 4,166,112).

Other *Bacillus thuringiensis* strains specific for dipteran pests have also been described. A *Bacillus thuringiensis* isolate has been disclosed which is toxic to Diptera and Lepidoptera (Hodgman et al., 1993, FEMS Microbiology Letters 114:17-22). Sodium dodecyl polyacrylamide gel electrophoresis (SDS-PAGE) of the purified crystal delta-endotoxin from this isolate revealed three protein species which are related to Cry1Ab, Cry1B, and Cry2A toxins. There has also been disclosed a *Bacillus thuringiensis* isolate which produces a dipteran-active crystal comprised of proteins with molecular weights of 140, 122, 76, 72, and 38 kDa (Payne, 1994, U.S. Pat. No. 5,275,815). EP 480,762 discloses five B.t. strains which are each active against dipteran pests; each also has a unique crystal delta-endotoxin pattern.

Several *Bacillus thuringiensis* strains have been described which have pesticidal activity against pests other than Lepidoptera, Coleoptera, and Diptera. Five *Bacillus thuringiensis* strains have been disclosed which produce delta-endotoxins that are toxic against nematodes (Edwards, Payne, and Soares, 1988, Eur. Pat. Appl. No. 0 303 426 B1). There has also been disclosed a *Bacillus thuringiensis* strain, PS81F, which can be used to treat humans and animals hosting parasitic protozoans (Thompson and Gaertner, 1991, Eur. Pat. Appl. No. 0 461 799 A2). Several *Bacillus thuringiensis* isolates have also been disclosed with activity against acaride pests. These isolates produce crystals comprised of proteins with molecular weights in the range of 35 kDa to 155 kDa (Payne, Cannon, and Bagley, 1992, PCT Application No. WO 92/19106). There have also been disclosed *Bacillus thuringiensis* strains with activity against pests of the order Hymenoptera (Payne, Kennedy, Randall, Meier, and Uick, 1992, Eur. Pat. Appl. No. 0 516 306 A2); Hemiptera (Payne and Cannon, 1993, U.S. Pat. No. 5,262,159); fluke pests (Hickle, Sick, Schwab, Narva, and Payne, 1993, U.S. Pat. No. 5,262,399); and pests of the order Phthiraptera (Payne and Hickle, 1993, U.S. Pat. No. 5,273,746). Furthermore, another strain of *Bacillus thuringiensis* subsp. *kurstaki*, WB3S-16, isolated from Australian sheep wool clippings, has been disclosed that is toxic to the biting louse *Damalinia ovis*, a Phthiraptera pest (Drummond, Miller, and Pinnock, 1992, *J. Invert. Path.* 60:102-103).

The delta-endotoxins are encoded by cry (crystal protein) genes which are generally located on plasmids. The cry genes have been divided into more than 50 classes and several subclasses based on relative amino acid homology and pesticidal specificity. The major classes are Lepidoptera-specific (cry1); Lepidoptera- and Diptera-specific (cry2); Coleoptera-specific (cry3); Diptera-specific (cry4) (Hofte and Whiteley, 1989, Microbiological Reviews 53:242-255); Coleoptera- and Lepidoptera-specific (referred to as cry5 genes by Tailor et al., 1992, Molecular Microbiology 6:1211-1217); and Nematode-specific (referred to as cry5 and cry6 genes by Feitelson et al., 1992, Bic)/Technology 10:271-275). A current list of cry toxins can be found, for example, in Crickmore, N., Zeigler, D. R., Schnepf, E., Van Rie, J., Lereclus, D., Baum, J, Bravo, A. and Dean, D. H. "*Bacillus thuringiensis* toxin nomenclature" (2009); Revision of the Nomenclature for the *Bacillus thuringiensis* Pesticidal Crystal Proteins, N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813.

Delta-endotoxins may or may not be in crystal form, and have been produced by recombinant DNA methods.

There is a continued need for the identification of novel *B. thuringiensis* strains which display a broader or different spectrum of, or an increased level of pesticide activity.

SUMMARY OF THE INVENTION

The present invention generally relates to a novel biologically pure bacterial strain of *Bacillus thuringiensis*, VBTS 2528. This strain has been deposited with the American Type Culture Collection (ATCC) under Accession No. PTA-120423.

The bacterial strain may be further characterized by its possession of a novel combination of cry genes, namely, the presence of cry1Ac, cry1Ca, and cry2Aa genes in a single strain. The invention further relates to a biologically pure bacterial culture of a *Bacillus thuringiensis* VBTS 2528.

The invention further relates to a pesticidal composition comprising VBTS 2528 or a mutant thereof which retains the pesticidal activity of VBTS 2528 and a suitable carrier.

The invention further relates to methods for controlling insect pests comprising applying to an infested area a pesticidally effective amount of VBTS 2528 or a mutant thereof which retains the pesticidal activity of VBTS 2528. Insects which can be treated with VBTS 2528 may belong to, but are not limited to, the following genera: *Spodoptera, Plutella, Trichoplusia, Heliothis, Agrotis, Cydia, Anticarsia, Lymantria*, and *Choristoneura*. Specific insect species include, but are not limited to, *Plutella xylostella* (diamondback moth), *Trichoplusia ni* (cabbage looper), *Spodoptera exigua* (beet armyworm), *Heliothis virescens* (tobacco budworm), *Spodoptera frugiperda* (fall armyworm), *Agrotis ipsilon* (black cutworm), *Cydia pomonella* (codling worm), *Anticarsia gemmatalis* (velvetbean caterpillar), *Lymantria dispar* (gypsy moth), and *Choristoneura fumiferana* (spruce budworm).

DETAILED DESCRIPTION OF THE INVENTION

The invention generally relates to a novel biologically pure bacterial strain of *Bacillus thuringiensis*, VBTS 2528. VBTS 2528 has been deposited with the American Type Culture Collection (ATCC) under Accession No. PTA-120423. VBTS 2528 exhibits improved pesticide activity as compared to other *B. thuringiensis* strains. The phrase "biologically pure bacterial strain" as used herein means a strain essentially free from biological contamination and having a genetic uniformity such that different substrains taken therefrom will display substantially identical genotypes and phenotypes.

The terms "isolate" and "strain" are used interchangeably in this application.

A plasmid array, or profile, which is readily obtainable, for example, by electrophoretic separation of bacterial plasmids, may serve to characterize the genetic architecture of a strain and thus serve as a further identifier of the bacterial isolate of the invention. A representative plasmid profile obtained from *B. thuringiensis* VBTS 2528 is shown in FIG. 1.

Figure 1:
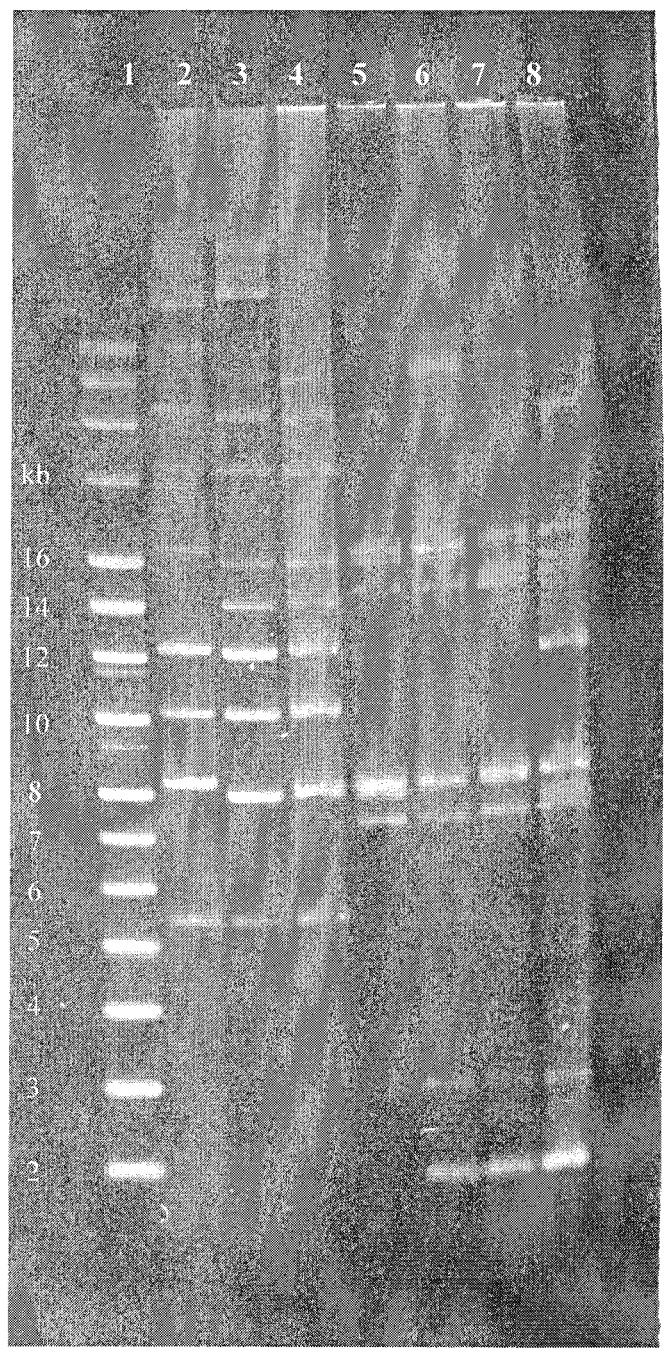
FIG. 1 is a photograph of an agarose gel containing a set of plasmid profiles for *B. thuringiensis* VBTS 2528 and several reference strains.

In addition to the plasmid profile of FIG. 1, strain VBTS 2528 is identifiable by the presence of genes encoding Cry1Ac, Cry2Aa and Cry1Ca endotoxin proteins.

VBTS 2528 strain of *B. thuringiensis* may be isolated using a method disclosed in the present invention or a variation of the method. The method comprises the steps of first identifying a combination of genes coding for endotoxin proteins, the presence or absence of which is determinative of toxicity towards a particular target pest; next, pre-screening or isolating from among available *B. thuringiensis* strains a set of variants which contain that combination of endotoxin genes; and then screening that set of variants to obtain a preferred isolate. The identification of particular endotoxin gene combinations, and the ability of the corresponding toxin complexes to produce differential toxicity against different target pests, may be accomplished by comparing the toxicity of strains which synthesize certain toxins with others which do not. If necessary, genes responsible for the production of toxins of interest may be selectively removed, for example, by heat curing, and the resulting strains tested for enhancement or diminution of toxicity.

The desirable presence of cry1Ac, cry2Aa and cry1Ca genes may be identified using nucleotide probes capable of hybridizing with these genes. A number of toxin genes, including but not limited to, cry1Aa, cry1Ab, cry1Ac, cry1Ba, cry1Ca, cry1Da, cry1Aa, cry1Fa, cry1Ga, cry1Ha, cry1Ia, cry2Aa, cry 2Ab, cry3Aa, cry3Ba, cry4Aa, cry4Ba have been identified, and partial or entire sequences thereof have been published, for example, by Schnepf et al in J. Biol. Chem., 260:6264-6272 (1985). It has been found that certain regions of these genes are highly conserved, permitting the preparation of a DNA probe which recognizes *B. thuringiensis* endotoxin genes in general. Such a generalized probe, when hybridized with the genome of a strain which through routine screening has been found to have some degree of toxicity towards a pest species of interest, may then be used to identify and characterize the endotoxin genes present in that type strain. These manipulations, as well as others which are useful in the practice of the present invention, may be accomplished using techniques which are well-known and can be found in references such as Maniatis et al., Molecular Cloning, A Laboratory Manual, Cold Spring Harbor Laboratory, 1982, or current edition. One example of a generalized probe, used to identify the genes cry1Aa, cry1Ab, cry/C and cry1D which appear to confer improved toxicity characteristics upon *B. thuringiensis*, is the probe described in U.S. Pat. No. 5,801,046 as SEQ ID NO:1.

Once a particular combination of endotoxin genes has been identified, *B. thuringiensis* VBTS 2528 which contains cry1Ac, cry1Ca and cry2Aa genes and is thus capable of producing the corresponding combination of endotoxin proteins, may be isolated. The isolation may be accomplished by preparing a set of gene-specific nucleotide probes which are capable of hybridizing with cry1Ac, cry2Aa and cry1Ca gene sequences. These unique sequences are obtained from what have been described as highly variable (i.e., non-conserved) regions of the *B. thuringiensis* δ-endotoxin genes. As in the case of the generalized probes described above, the construction of gene-specific probes may be accomplished by reference to published nucleotide sequences.

The gene specific probes used for identifying these genes are as follows:

```
Cry1Ac Probe (SEQ ID NO: 1):
5'GCTACGTCATTAGATAATCTACAATCAAGTGATTTTGGTTATTTT
GAAAGTGCCAATGCTTTTACATCTTCATTAGGTAATATAGTAGGTCT
TAGAAATTTTAGTGGGACTGCAGGAGTG 3'

Cry1Ca Probe (SEQ ID NO: 2):
5'CGGGGATTAAATAATTTACCGAAATCTACGTATCAAGATTGG 3'

Cry2Aa Probe (SEQ ID NO: 3):
5'GACTAATCTCAATCACAACTTTAATTGCAGCACGGTCCTCCCTC
CTTTATCAACACC 3'
```

These sequences may be used in their entirety, or may be shortened, lengthened or internally modified to obtain probes possessing the desired degree of homology to, and corresponding hybridization specificity for, the endotoxin genes sought to be identified. Moreover, new probes for identifying these genes may be derived which may be employed without departing from the practice of the method of the present invention.

The above gene-specific probes, which may be labeled in a number of conventional ways to permit assessment of their binding, can then be used to rapidly and economically pre-screen all available strains of *B. thuringiensis*. This pre-screening may be carried out using well-known techniques such as replica plating, hybridization, autoradiography and the like. In this manner, one may easily select, from among the strains being tested, a set of variants which demonstrate a pattern of hybridization representative of the gene complement being sought.

From the variants selected by pre-screening, *B. thuringiensis* VBTS 2528 strain may be identified by conventional small-scale screening for toxicity. The isolate ultimately selected may then be optimized for toxin production using known techniques of yield improvement or by the manipulation of the strain itself, such as by the production of mutants, transconjugants, recombinants, or genetically engineered derivatives thereof. Such manipulation may also include the preparation of a preferred phenotype of the selected isolate, for example, a spo⁻ (asporogeneous) mutant which produces a toxin crystal but no spores. Accordingly, in one aspect, the invention relates to the isolate *B. thuringiensis* VBTS 2528 or a mutant, transconjugant, recombinant, or genetically engineered derivative thereof.

Yet another identifying characteristic of *B. thuringiensis* VBTS 2528 strain is that this strain may have additional toxin genes which are yet unidentified. This hypothesis is based on the small peaks in the HPLC profile of VBTS 2528 that align closely with the Cry1Aa and Cry1Ab toxins present for HD-1 and ABTS 1857 strains. However, gene probe data for VBTS 2528 indicates that VBTS 2528 does not have cry1Aa or cry1Ab genes.

In yet another aspect, the present invention relates to a biologically pure bacterial culture of *B. thuringiensis* VBTS 2528. The phrase "biologically pure culture" as used herein means a culture essentially free from biological contamination and having a genetic uniformity such that different sub-cultures taken therefrom will display substantially identical genotypes and phenotypes. Such cultures may be useful in large-scale fermentation or, alternatively, as the starting material for well-known strain manipulation techniques. Accordingly, mutants, transconjugants, recombinants, and genetically engineered variants which are derived from VBTS 2528 and cultures thereof are within the scope of the invention.

In another aspect of the present invention, compositions are disclosed comprising a pesticidally effective amount of *B. thuringiensis* VBTS 2528, or an endotoxin obtained therefrom, in a suitable form for direct application in combination with a suitable carrier. It is well understood by a person of skill in the art that a pesticidally effective amount will vary depending on such factors as, for example, the specific insects to be controlled, the specific plant to be treated and method of applying the insecticidally active compositions. For example, the compositions may require dilution with a suitable quantity of water or other diluent before application. The carrier is preferably inert. The pesticidal concentration may vary depending upon the nature of the particular formulation, specifically, whether it is a concentrate or a ready-to-use formulation. The composition may contain from about 0.1% by weight to about 99% by weight, preferably from about 0.1% by weight to about 95% by weight of VBTS 2528, mutant or variant of the present invention, from about 1% to about 98% by weight of an acceptable solid or liquid inert carrier, and from about 0 to about 50% by weight, preferably from about 0.1% to about 50% by weight of a surfactant. These compositions may be administered at about 0.01 lb-5.0 lb per acre when in dry form and at about 0.01-10 pints per acre when in liquid form.

After identification and stabilization of *B. thuringiensis* VBTS 2528 strain according to the above methodology, large-scale fermentation may be carried out using media and fermentation techniques which are standard in the industry. The endotoxin crystals (together with the spores, from which the crystals are not readily separable) may then be separated from the fermentation broth and lyophilized or formulated in any of a number of well-known ways, including as a liquid concentrate, dry or wettable powder or suspension for spraying on or under foliage, and a granular preparation for application to soil. The phrase "acceptable carrier" as used herein means an otherwise inert filler or excipient which confers upon the composition desirable storability, material handling and application characteristics; commonly-used carriers may include fillers, binders, surfactants, dispersants, adhesion agents and the like.

The pesticidal compositions comprising *B. thuringiensis* VBTS 2528 strain, may be in a form of, for example, a suspension, a dispersion, an aqueous emulsion, a dusting powder, a dispersible powder, an emulsifiable concentrate, an aerosol or micro or macroencapulated granules or any other formulation that gives controlled release of *Bacillus thuringiensis*. Such compositions may be obtained by the addition of a surface active agent, e.g., a dispersing agent, emulsifying agent or wetting agent, or an inert carrier or other component to facilitate handling and application for particular target pests.

Suitable surface-active agents include anionic compounds such as a carboxylate, for example, a metal carboxylate of a long chain fatty acid; a N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl-naphthalene sulphonate; salts or sulphonated naphthalene-formaldehyde condensates or salts of polyacrylic acid; salts of sulphonated phenol-formaldehyde condensates; or more complex sulphonates such as the amide sulphonates, e.g., the sulphonated condensation product of oleic acid and N-methyl taurine or the dialkyl sulphosuccinates, e.g., the sodium sulphonate or dioctyl succinate. Non-ionic agents include condensation products of fatty acid esters, fatty alcohols, fatty acid amides or fatty-alkalyl- or alkenyl-substituted phenols with ethylene oxide and/or propylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include inorganic minerals such as phyllosilicates, carbonates, sulfates, phosphates; organic materials such as sugar, starches, or cyclodextrins; or botanical materials such as powdered corncobs, rice hulls, walnut shells, cornmeal, pelleted grains, and cellulosic fibers.

In a further embodiment, pesticidal compositions of the present invention can be treated prior to formulation to prolong the pesticidal activity when the cells are applied to the environment of a target pest. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropranol and ethanol; histological fixatives, such as Bouin's fixative and Helly's fixative (see, for example, Humason, Animal Tissue Techniques, W. H. Freeman and Co., 1967); preservatives; UV sunscreens; spray adjuvants (humectants); antifoams; and stickers.

The pesticidal compositions of the invention can be applied directly to the plant by, for example, spraying or dusting a pesticidally effective amount of VBTS 2528 or a mutant thereof which retains the pesticidal activity of VBTS 2528 at the time when the pest has begun to appear on the plant or before the appearance of pests as a protective measure. Plants to be protected within the scope of the present invention include, but are not limited to, cereals (wheat, barley, rye, oats, rice, sorghum and related crops), beet (sugar beet and fodder beet), drupes, pomes and soft fruit (apples, pears, plums, peaches, almonds, cherries, strawberries, raspberries, and blackberries, tomatoes), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, potatoes, paprika), lauraceae (avocados, cinnamon, camphor), deciduous trees and conifers (linden-trees, yew-trees, oak-trees, alders, poplars, birch-trees, firs, larches, pines), or plants such as maize, tobacco, nuts, coffee, sugar cane, tea, vines hops, bananas and natural rubber plants, as well as ornamentals. The preferred mode of application is by foliar spraying. It is generally important to obtain good control of pests in the early stages of plant growth as this is the time when the plant can be most severely damaged. The spray or dust can conveniently contain another insecticide or pesticide, e.g., fungicide, grass herbicide or fertilizer, if this is thought necessary. In a preferred embodiment, the composition of the invention is applied directly to the plant The compositions of the present invention may be effective against pests of the order Lepidoptera, e.g., *Achroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylis hospes, Colias eurytheme, Corcyra cephalonica, Cydia latiferreanus, Cydia pomonella, Datana integerrima, Dendrolimus sibericus, Desmiafuneralis, Diaphania hyalinata, Diaphania nitidalis, Diatraea grandiosella, Diatraea saccharalis, Ennomos subsignaria, Eoreuma loftini, Ephestia elutella, Erannis tiliaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrsisalis, Malacosoma* sp., *Mamestra brassicae, Mamestra configurata, Manduca quinquemaculata, Manduca sexta, Maruca testulalis, Melanchra picta, Operophtera brunata, Orgyia* sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota sultana, Platyptilia carduidactyla, Plodia interpunctella, Plutella xylostella, Pontia protodice, Pseudaletia unipuncta, Pseudoplusia includens, Sabulodes aegrotata, Schizura concinna, Sitotroga cerealella, Spilonota ocellana, Spodoptera* sp., *Syngrapha falcifera, Thaurnstopoea pityocampa, Tineola bisselliella, Trichoplusia ni, Udea rubigalis, Xylomyges curialis, Yponomeuta padella*. The compositions of the invention may also be effective against insect pests of the order Coleoptera, e.g., *Leptinotarsa* sp., *Acanthoscelides obtectus, Callosobruchus chinensis, Epilachna varivestis, Pyrrhalta luteola, Cylas formicarius elegantulus, Listronotus oregonensis, Sitophilus* sp., *Cyclocephala borealis, Cyclocephala immaculata, Macrodactylus subspinosus, Popillia japonica, Rhizotrogus majalis, Alphitobius diaperinus, Palorus ratzeburgi, Tenebrio molitor, Tenebrio obscurus, Tribolium castaneum, Tribolium confusum, Tribolius destructor*, Diptera, e.g., *Aedes* sp., *Andes vittatus, Anastrepha ludens, Anastrepha suspensa, Anopheles barberi, Anopheles quadrimaculatus, Armigeres subalbatus, Calliphora stygian, Calliphora vicina, Ceratitis capitata, Chironomus tentans, Chrysomya rufifacies, Cochliomyia macellaria, Culex* sp., *Culiseta inornata, Dacus oleae, Delia antiqua, Delia platura, Delia radicum, Drosophila melanogaster, Eupeodes corollae, Glossina austeni, Glossina brevipalpis, Glossina fuscipes, Glossina morsitans centralis, Glossina morsitans morsitans, Glossina morsitans submorsitans, Glossina pallidipes, Glossina palpalis gambiensis, Glossina palpalis palpalis, Glossina tachinoides, Haemagogus equinus, Haematobia irritans, Hypoderma bovis, Hypoderma lineatum, Leucopis ninae, Lucilia cuprina, Lucilia sericata, Lutzomyia longlpaipis, Lutzomyia shannoni, Lycoriella mali, Mayetiola destructor, Musca autumnalis, Musca domestica, Neobellieria* sp., *Nephrotoma suturalis, Ophyra aenescens, Phaenicla sericata, Phlebotomus* sp., *Phormia regina, Sabethes cyaneus, Sarcophaga bullata, Scatophaga stercorarla, Stomaxys calcitrans, Toxorhynchites amboinensis, Tripteroides bambusa; Acari*, e.g., *Oligonychus pratensis, Panonychus ulmi, Tetranychus urticae; Hymenoptera*, e.g., *Iridomyrmex humilis, Solenopsis invicta; Isoptera*, e.g., *Reticulitermes hesperus, Reticulitermes flavipes, Coptotermes formosanus, Zootermopsis angusticollis, Neotermes connexus, Incisitermes minor, Incisitermes immigrans; Siphonaptera*, e.g., *Ceratophyllus gallinae, Ceratophyllus niger, Nosopsyllus fasciatus, Leptopsylla segnis, Ctenocephalides canis, Ctenocephalides*

*felis, Echicnophaga gallinacea, Pulex irritans, Xenopsylla cheopis, Xenopsylla vexabilis, Tunga penetrans*; and *Tylenchida*, e.g., *Melodidogyne incognita, Pratylenchus penetrans*.

The following examples are presented by way of illustration and are not intended to limit the invention in any way.

Example 1

Construction of VBTS 2528

The new strain of *B. thuringiensis*, VBTS 2528, has been constructed using well-known transconjugation techniques. These techniques are described, for example, in U.S. Pat. Nos. 4,935,353 and 5,080,897. Precursor strain VBTS 2517 was used to create VBTS 2528 strain. VBTS 2528 strain is a single colony isolated from VBTS 2517. VBTS 2517 has been deposited with the ATCC under Accession No. SD-6212. VBTS 2528 has been deposited with the ATCC under Accession No. PTA-120423.

a) Construction of Precursor VBTS 2517 Strain

VBTS 2517 was constructed using VBTS 2436 and ABTS 7655 strains.

VBTS 2436 is one of the two isolates derived from ABTS 8019, natural isolate from the Abbott Laboratories, now Valent BioSciences Corporation, strain collection. ABTS 8019 was originally isolated from hickory leaf in Bristol, Wis. Using gene specific probes with known toxins, ABTS 8019 appeared to have the same genes as HD-1, a Bt strain of variety kurstaki (flagellar serotype 3ab). HPLC analysis of ABTS 8019 demonstrated that it had approximately half the total protein as HD-1, that its highest percentage of toxin was probably 1Ac or 1Ac-related, and that it had a much smaller percentage of 1Ab. As part of the characterization process, ABTS 8019 was streaked out and individual isolates were directly analyzed for their protein content fractions. Based upon the presence or absence of a 56 kDa band, two derivative strains were isolated and renamed. The derivative which was missing the 56 kDa band was named VBTS 2436. VBTS 2436 was approximately equivalent in its activity against *S. exigua* to HD-1. Unlike HD-1, VBTS 2436 had approximately equal proportions of 135 kDa (Cry1A) and 60 kDa (Cry2A) protoxins. HPLC data demonstrated that the 135 kDa band had all three toxins (Cry1Aa, Cry1Ab, Cry1Ac) found in HD-1. VBTS 2436 has higher proportions of both cry1Ac and cry2Aa toxins compared to HD-1. VBTS 2436 has been deposited with the ATCC under Accession No. SD-6213.

ABTS 7655 was originally isolated from an insect cadaver found in Greenville, Miss. This strain has a typical gene profile of Bt aizawai strains (cry1Aa, cry1Ab, cry1Ca, cry1Da, cry2Ab). It was not substantially more active than the strain ABTS1857, described in U.S. Pat. No. 5,801,046. During transconjugation experiments, it was determined that ABTS 7655 differed from other common aizawai type strains, in that cry1Ca and cry1Da genes were not transferred together. This finding implied that a cry1Ca gene was located on a separate plasmid, unlike in ABTS1857 or other published aizawai strains. ABTS 7655 has a higher proportion of cry1Ca compared to ABTS 1857 based upon HPLC data. ABTS 7655 has been deposited with the ATCC under Accession No. SD-6214.

Strains VBTS 2436 and ABTS 7655 were transconjugated as follows: The two strains were inoculated from slants into separate 250 ml flasks containing 50 ml of Luria Broth (LB) medium and shaken at 250 rpm at 28-30° C. until they reached mid-log phase ($OD_{600}$ of 0.4 to 0.6). Targeting 50 mcl per strain, approximately the equivalent number of cells was calculated for each strain based upon the OD readings. The calculated amounts were pipetted sequentially onto a sterile 0.2μ pore-size Biotrans nylon membrane circle (ICN), 4 cm in diameter, which had been placed onto a sterile Whatman 1 filter of a larger size on a Luria agar plate. The plate was incubated at 28-3000 overnight until growth was apparent on the membrane filter. The filter was then transferred to a 50 ml sterile capped tube containing 5 ml of LB and vortexed to disperse the cells. The sample was serially diluted, then plated onto nutrient agar plates, to obtain approximately 700 distinct colonies for screening. Plates were incubated overnight at 28-30° C.

Colony screening was performed by transferring cells using sterile toothpicks from individual colonies to LB contained in sterile 96-well microtiter plates. Two wells on each plate were inoculated with control strains, HD-1 (cry1Ac, cry2Aa) and ABTS 1857 (cry1Ca). Seven microtiter plates, with a total of 658 colonies were incubated at 28° C., overnight. For each plate, 3 OmniTrays™ (Nunc) containing Luria agar and a Biotrans™ nylon membrane (ICN, 8×12 cm, 1.2μ pore size) were prepared. An additional OmniTray™ with agar only was prepared to serve as a "Master" plate. Sterile 96-pin replicators were used to transfer colonies from the wells to the 3 membranes and the master plate. Plates were allowed to grown at 28° C. for approximately 16 hours. Membranes were inspected for growth and those wells that did not show growth were noted. Membranes were transferred, colony side up, to 5 ml puddles of TES buffer (30 mM Tris-HCl pH7.5, 5 mM EDTA pH 7.5, 50 mM NaCl) containing 5 mg/ml lysozyme added just prior to use, for one hour. The membranes were washed twice, with agitation for 20 minutes each time, in a dish containing excess amounts (at least 10 ml/filter) of denaturing solution (0.5M NaOH, 2.5M NaCl). Two more washes were performed in the same manner using neutralizing solution (0.5M Tris pH 7.0, 3.0 M NaCl). After briefly drying on blotting paper, the filters were baked in an 80° C. oven for 1-2 hours.

DNA hybridization was carried out using labeled DNA probes for cry1Ac, cry1Ca, and cry2Aa. The probes were radioactively end-labeled with gamma-$AT^{32}P$ (3000 Ci/mmol) using standard labeling procedures. Membrane filters were sorted into heat sealable pouches and prehybridized at 58° C. for 1 hour in prehybridization buffer (6×SSC, 5×Denhardt's solution, 10 mM $KPO_4$ pH7.2, 0.1% SDS, 0.025% DNA free acid) after which radioactive probe was added to each. The pouches were resealed and hybridized at 58° C. overnight. Filters exposed to the same probe were combined, and moved to clean pouches containing wash buffer (2×SSC, 0.1% SDS). The filters were washed three times: once at room temperature, then twice at 58° C. for 1 hour each, changing wash buffer each time and with occasional agitation. The filters were dried on absorbant paper briefly before being exposed to XAR film with intensifying screens for up to 5 days, after which the positive spots, indicating gene presence, were scored.

DNA hybridization results indicated that all three genes were present in six transconjugants from strains VBTS 2436 and ABTS 7655. These isolates were streaked again to obtain single isolates. Six isolates from each of the six transconjugants were screened again using hybridization to confirm genotypes. Three colonies with confirmed genotypes from each of the six transconjugants were pooled and given experimental strain IDs (499-7 through 499-12). Flask cultures of these strains and HD-1 and 1857 controls were tested for activity against *T. ni* and *S. exigua*, as well as for protein using both SDS-PAGE and HPLC.

Based upon these results, experimental strain 499-12 was chosen for scale-up testing and placed in the culture collection designated as VBTS 2517.

b) Construction of VBTS 2528 Strain

VBTS 2517 was grown under production conditions in 7.5 L fermentors, initially using inoculum culture prepared from agar slants. When frozen inoculum culture was used, bioactivity was reduced, compared to those fermentations where the inoculum culture was derived from slants. Growing the inoculum preparations longer before freezing did not substantially improve insect potency. VBTS 2517 was streaked onto a nutrient agar plate to obtain single colonies. Five colonies were selected and confirmed by DNA hybridization to have cry1Ac, cry1Ca, and cry2Aa genes. Flask cultures from these five isolates were prepared and screened for activity against *T. ni* and *S. exigua*. Based upon those results, experimental isolate 753-A3 was chosen and designated VBTS 2528. Multiple experiments in fermentors confirmed frozen inoculum of VBTS 2528 gave broths with equal or higher activity against cabbage loopers when compared to VBTS 2517 inoculum from slants.

Example 2

Characterization of VBTS 2528 a) Plasmid Profile of VBTS 2528 and Control Strains

Plasmids were prepared from flask cultures of strains VBTS 2528, parent strains ABTS 7655, and VBTS 2436, control strains HD-1 and ABTS 1857, and competitor product isolates from CoStar® and Agree® products using the Qiagen HiSpeed® Plasmid Maxi Kit with modifications for *Bacillus thuringiensis* strains as described. Buffers were provided in the kit. Strains were grown overnight in 10 ml of LB (Luria broth) medium at 28-30° C. with shaking at 220 rpm. The culture was diluted 1:100 into 100 ml of LB medium in a 500 ml flask and grown for 4 hours with shaking at 220 rpm. The cells were harvested by centrifugation at 3000×g for 15 minutes at 4° C. The pellets were resuspended in 20 ml of Resuspension Buffer (P1) containing freshly added 100 µg/ml RNAse A and 5 mg/ml lysozyme and incubated at 37° C. for 1 hour with vigorous shaking (220 rpm). To each sample, 20 ml of Lysis Buffer (P2) was added, followed by mixing by inversion 4-6 times until culture turned blue due to the presence of a color indicator in Buffer P1. Then, 20 ml of chilled Neutralization Buffer (P3) was added and the sample mixed by inversion as before. A brief low speed centrifugation was done for 10 minutes to assist in pelleting the precipitate to obtain a clear lysate. 10 ml of each lysate was applied to a Qiafilter Cartridge and incubated at room temperature for 10 minutes. A plunger was inserted into the Qiafilter Cartridge and the lysate was filtered into a HiSpeed® Maxi Tip previously equilibrated with 10 ml of Buffer QBT. The lysate was allowed to enter the resin by gravity flow after which it was washed with 60 ml of Buffer QC. The plasmid DNA was eluted with 15 ml of Buffer QF. The plasmid DNA was precipitated by adding 10.5 ml of room temperature isopropanol, incubating for 5 minutes, and then passing the sample through a QIAprecipitator. The samples were washed and dried by first passing 70% ethanol through the QIAprecipitator and then passing air. The precipitator unit was attached to a 5 ml syringe and held over a 1.5 ml collection tube. 1 ml of Buffer TE was added to the syringe and pushed through the QIAprecipitator to elute the DNA. The eluate was added back into the syringe and pushed through a second time to complete recovery of the plasmid.

Thirty microliters of each plasmid sample was concentrated by centrifugation under vacuum until nearly dry. The samples were resuspended in 12 µl TE buffer. 4 µl of each sample was mixed with 2 µl of gel tracking buffer (15% Ficoll 400, 0.25% bromophenol blue) prior to loading 6 µl onto a 0.5% Gold Agarose gel (Seakem®) prepared in 0.5×TBE buffer. 3 µl of Supercoiled DNA Marker (Invitrogen) was included as a size standard. The gel (20 cm×10 cm) was run for approximately 15 minutes at 20 mA (~110V) and then reduced to 45V for approximately 16 hours. The gel was stained for 20 minutes in 0.5 µg/ml ethidium bromide in 0.5×TBE buffer and destained for approximately 40 minutes in 0.5×TBE buffer. The gel was photographed on a UV light box with an orange filter at F4.5 for 2.5 seconds.

Plasmid profiles clearly show that strain VBTS 2528 has a distinct profile relative to its parent strains and strains isolated from commercial products. FIG. 1 is a photograph of the gel containing a set of plasmid profiles for *B. thuringiensis* VBTS 2528 and several reference strains.

The description of the gel is as follows:

lane 1 is supercoiled DNA Ladder (obtained from Invitrogen);

lane 2 is Agree® isolate (obtained from Certis USA, LLC). This is a transconjugant strain with cry1Ac and cry1Ca, but not cry2Aa.

lane 3 is ABTS 1857, XenTari strain;

lane 4 is ABTS 7655, a parent strain of VBTS 2528;

lane 5 is VBTS 2528;

lane 6 is VBTS 2436, a parent strain of VBTS 2528;

lane 7 is HD-1, DiPel strain; and lane 8 is CoStar® isolate (obtained from Certis USA, LCC) with cry1Ac and cry2Aa, but not cry1Ca.

b) SDS-PAGE Electrophoresis of VBTS 2528 Isolate and HD-1 Control

Two VBTS 2528 broth samples (J and K) were analyzed by SDS-PAGE for the presence or absence of the 60 kDa protein band, typically seen in DiPel. DiPel Standard powder 81-030-BD was included for comparison. Approximately 75 mg of 2528 whole broth product sample and approximately 30 mg of DiPel standard were weighed into microfuge tubes. Each was washed by adding 1 ml of 1M NaCl-5 mM EDTA pH 8.0, followed by centrifugation at 14,000×g for 5 minutes at 5° C. A second wash was done in 5 mM EDTA pH 8.0 and the pellet was resuspended with 5 mM EDTA pH 8.0 to a volume of 1 ml. A 100 µl aliquot of each washed sample and aliquots of washed DiPel standard of 180, 90, and 30 µl were centrifuged as before and the resulting pellets suspended in 200 µl sample buffer C (8M Urea, 0.05M CAPS, 2% (w/v) SDS, with 20 mM DTT (added just prior to use.)) The samples were boiled 8 minutes, after which an equal volume of Sample buffer D (0.25M Tris, 2% (w/v) SDS, 40% (v/v) glycerol, 20 mM DTT (added just prior to use)) was added. The samples were briefly centrifuged prior to loading 5 µl of supernatant onto an 8-16% Tris-glycine denaturing gel (Invitrogen). A molecular weight standard, Mark12™ (Invitrogen), was also loaded. After electrophoresis, the gel was stained using Colloidal Blue® Coomassie stain (Invitrogen) and destained in water. The protein bands were imaged using a BioRad GS710 densitometer. The 135 kDa (Cry1A) band and 60 kDa (Cry2A) bands were visible on the gel.

Figure 2:
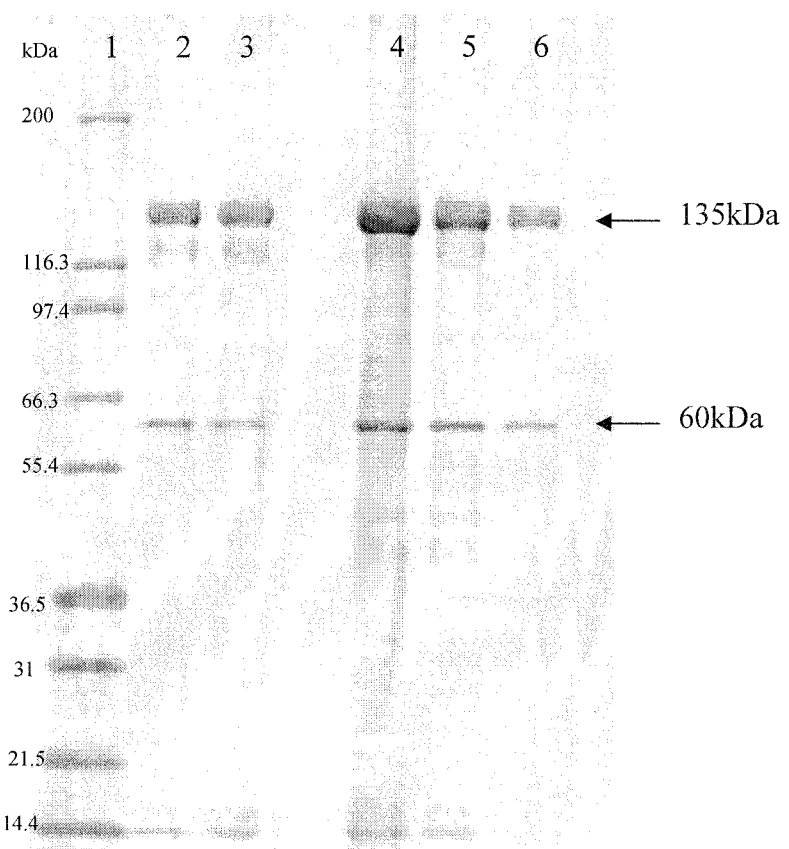
FIG. 2 is a photograph of the SDS-PAGE electrophoresis which shows the protein array of *B. thuringiensis* VBTS 2528 and the DiPel Strain, HD-1.

SDS-PAGE clearly shows that VBTS 2528 has appropriately sized protein bands for Cry1Ac, Cry1Ca, and Cry2Aa protoxins. FIG. 2 is a photograph of the SDS-PAGE electrophoresis which shows the protein array of *B. thuringiensis* VBTS 2528 and the DiPel Strain, HD-1.

Lane 1. Mark 12™ Molecular Weight Marker
Lane 2. VBTS 2528-J Broth Sample
Lane 3. VBTS 2528-K Broth Sample
Lane 4. DiPel Standard 3.8 mcg protoxin
Lane 5. DiPel Standard 1.91 mcg protoxin
Lane 6. DiPel Standard 0.64 mcg protoxin c) HPLC Profile of VBTS 2528 Vs. HD-1 Control Ion exchange HPLC was carried out on fermented materials of VBTS 2528 and controls strain HD-1 using a proprietary procedure based on the U.S. Pat. No. 5,523,211. The used chromatographic method identified Cry1 toxins expressed by *Bacillus thuringiensis* genes. This technique involved solubilization of parasporal crystals followed by cleavage with a proteolytic enzyme and their separation by high performance anion-exchange liquid chromatography at a constant pH in excess of 10 in an increasing gradient of sodium chloride. The specific gradient conditions for the column were achieved by employing a series of buffers having increased concentrations of the salt and which were introduced at a predetermined time and rate. The resultant chromatogram for VBTS 2528 shows identifiable peaks of individual toxins Cry1Ca and Cry1Ac and relative proportions of toxins. Differentiation from strain HD-1, which has Cry1Aa, Cry1Ab, and Cry1Ac toxins, is clear.

Figure 3:
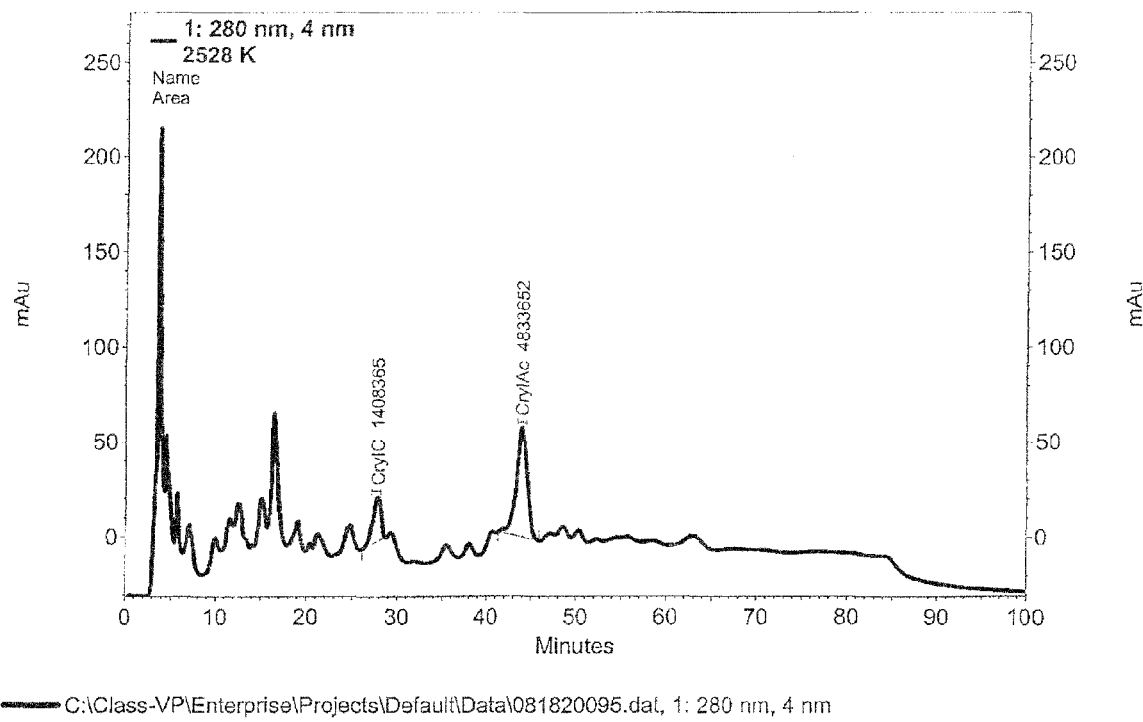
FIG. 3 describes the HPLC profile for *B. thuringiensis* VBTS 2528.
Figure 3:
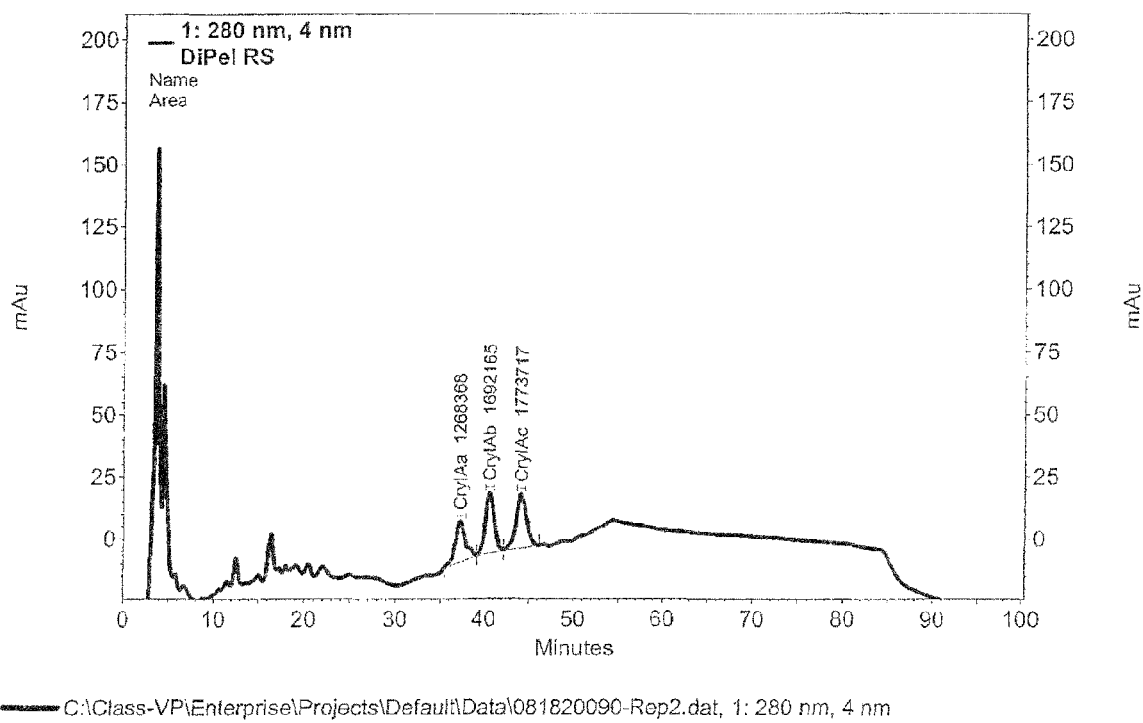

FIG. 3 depicts HPLC results, which indicate that VBTS 2528 produces the Cry1C and Cry1Ac toxins.

Bioassays were also carried out at Benzon Research Inc., PA. Preparations were incorporated into a Stoneville type general noctuid diet without antibiotics for velvetbean caterpillars and tobacco budworms. For gypsy moths and diamondback moths, species specific diets were used. For each replicate, six concentrations of each preparation were prepared. Untreated controls and reference standards were included with each replicate. Molten diet for each concentration and controls was dispensed into each of the 32 individual wells. For velvetbean caterpillar (*Anticarsia gemmatalis*), gypsy moth (*Lymantria dispar*), and tobacco budworm (*Heliothis virescens*), 1 unfed neonate larva was placed in each well containing solidified, treated diet. For the diamondback moth (*Plutella xylostella*), one third instar larvae was placed in each well. The diamondback moth strain used has demonstrated resistance to Btk. Test trays were held in a controlled-environment chamber at 27±1° C. and L:D 14:10 for 6 days from infestation prior to reading mortality. Mortality data from each of 3 or 4 replicates were separately analyzed using parallel probit analysis to provide LC50 estimates.

Table 1 demonstrates the results of bioassays of whole broth technical powders of VBTS 2517 as well as HD-1 and ABTS 1857 control strains from 7.5 L fermentors. The bioassay samples were grown in 7.5 L fermentors using production conditions. The fermentation broth was spray-dried without being concentrated. No formulation was done.

TABLE 1

| Ratio of LC50's | Cabbage looper | Diamondback moth | Btk- Res. Diamondback moth | Tobacco budworm | Gypsy moth | Velvetbean caterpillar |
|---|---|---|---|---|---|---|
| HD1/ 2517 | 2.47 | 2.45 | 9.16 | 2.68 | 2.02 | 2.01 |
| 1857/ 2517 | 2.99 | 7.2 | 1.30 | 1.98 | 6.08 | 3.90 |

Example 3

Bioassays of VBTS 2517 and VBTS 2528

Bioassays were carried out at Abbott Laboratories, IL using 4-day old *Trichoplusia ni* (cabbage looper), 4-day old *Plutella xylostella* (diamondback moth), All bacterial treatments were incorporated into the diet. Two or three replications were conducted for each study. Each replication tested seven dose levels of Bt whole culture and an untreated control. For *T. ni*, 30 larvae were tested per dose. For *P. xylostella*, 40 larvae were tested per dose. Insects were incubated at 28°±2° C. for *T. ni* and 25°±2° C. for *P. xylostella* with a 12-h light/12-h dark cycle for three days. Larval mortalities from the replications were pooled and using log-probit analysis, a single regression line was used to estimate the 50% lethal concentration ($LC_{50}$).

The results indicate that 2517 whole broth technical powder has more activity compared to HD-1 or ABTS 1857 whole broth technical powder against several insects.

Table 2 demonstrates the results of bioassays of two whole broth technical powders of VBTS 2528 from 30 L fermentors and DiPel (HD-1) concentrated technical powder from production level fermentors. The bioassay samples of VBTS 2528 were grown in 30 L fermentors using production conditions. The fermentation broth was spray dried without being concentrated and no formulation was done. The HD-1 control sample used for comparison was DiPel spray dried technical powder from concentrated production broth with no formulation.

TABLE 2

| Ratio of LC50's | Cabbage looper | Diamondback moth | Btk- Res. Diamondback moth | Tobacco budworm | Gypsy moth | Velvetbean caterpillar |
|---|---|---|---|---|---|---|
| HD1/ 2528-J | 1.39 | 0.98 | 17.2 | 2.15 | 1.06 | 0.89 |
| HD1/ 2528-K | 1.23 | 1.20 | 13.0 | 1.88 | 1.12 | 0.68 |

These results indicate that VBTS 2528 whole broth technical powder has equal or more activity than HD-1 concentrated technical powder against several insects.

We claim:

1. An isolated biologically pure bacterial strain of *Bacillus thuringiensis*, VBTS 2528, deposited with the American Type Culture Collection (ATCC) and having Accession No. PTA-120423.

2. An isolated biologically pure bacterial culture of a *Bacillus thuringiensis*, VBTS 2528.

3. The bacterial strain of claim 1 wherein said strain includes genes encoding cry1Ac, cry2Aa and cry1Ca endotoxin proteins.

4. A pesticidal composition comprising a mixture of the bacterial strain of claim 1 and a suitable carrier.

5. The pesticidal composition of claim 4, wherein said pesticidal composition comprises from about 0.1% to about 95% by weight of VBTS 2528, from about 1% to about 98% by weight of a solid or liquid inert carrier and from about 0.1% to about 50% by weight of a surfactant.

6. A method for controlling pests comprising applying to an infested area a pesticidally effective amount of the bacterial strain of claim 1.

7. The method of claim 6 wherein the pests are selected from the group consisting of *Spodoptera* genus, *Plutella* genus, *Trichoplusia* genus, *Heliothis* genus and *Agrotis* genus.

* * * * *